US012708733B2

(12) United States Patent
Kullik et al.

(10) Patent No.: US 12,708,733 B2
(45) Date of Patent: Aug. 18, 2026

(54) PROCESS FOR SUPPORTING BLOOD GAS EXCHANGE BY VENTILATION AND EXTRACORPOREAL BLOOD GAS EXCHANGE AND SYSTEM OPERATING ACCORDING TO THE PROCESS

(71) Applicant: Drägerwerk AG & Co. KGaA, Lübeck (DE)

(72) Inventors: Götz Kullik, Lübeck (DE); Tilman Von Blumenthal, Lübeck (DE); Bernd-Michael Dicks, Lübeck (DE)

(73) Assignee: Drägerwerk AG & Co. KGaA, Lübeck (DE)

(*) Notice: Subject to any disclaimer, the term of this patent is extended or adjusted under 35 U.S.C. 154(b) by 1094 days.

(21) Appl. No.: 17/257,049

(22) PCT Filed: May 24, 2019

(86) PCT No.: PCT/EP2019/063442

§ 371 (c)(1),
(2) Date: Dec. 30, 2020

(87) PCT Pub. No.: WO2020/007530

PCT Pub. Date: Jan. 9, 2020

(65) Prior Publication Data

US 2021/0170136 A1 Jun. 10, 2021

(30) Foreign Application Priority Data

Jul. 3, 2018 (DE) ......................... 102018005228.2

(51) Int. Cl.

*A61M 16/22* (2006.01)
*A61M 16/00* (2006.01)
*A61M 16/10* (2006.01)

(52) U.S. Cl.

CPC ........ *A61M 16/22* (2013.01); *A61M 16/0003* (2014.02); *A61M 2016/103* (2013.01);
(Continued)

(58) Field of Classification Search

CPC ................ A61M 60/113; A61M 16/22; A61M 2016/103; A61M 1/1601; A61M 16/0003; A61M 2205/3334; A61M 2205/3344
(Continued)

(56) References Cited

U.S. PATENT DOCUMENTS 5,810,759 A 9/1998 Merz
9,775,959 B2 * 10/2017 Kokko ............. A61M 16/0051
(Continued)

FOREIGN PATENT DOCUMENTS

CN 101002969 A 7/2007
EP 3291854 A1 3/2018
(Continued)

*Primary Examiner* — Rachel T Sippel
*Assistant Examiner* — Gwynneth L Howell
(74) *Attorney, Agent, or Firm* — McGlew and Tuttle, P.C.

(57) ABSTRACT

A system (10) for supporting the blood gas exchange of a patient (12) by means of a ventilator (14) as well as by a $CO_2$ removal device (16), and a process for operating such a system (10), wherein a measured value concerning an expiratory or end-expiratory $CO_2$ concentration in the breathing gas of the patient (12) can be detected by a sensor system (20), wherein a measured value can be selected as a start value by means of an operating action, wherein a trend parameter can be determined with the start value and with a respective, currently determined measured value and wherein a difference of a set point for the trend parameter and a respective, current value of the trend parameter can be fed to a controller (42), which acts on the $CO_2$ removal device.

20 Claims, 5 Drawing Sheets

(52) U.S. Cl.
CPC ... *A61M 2205/583* (2013.01); *A61M 2230/42* (2013.01); *A61M 2230/432* (2013.01)

(58) Field of Classification Search
USPC .................................................... 128/205.28
See application file for complete search history.

(56) References Cited

U.S. PATENT DOCUMENTS

| | | | | |
|---|---|---|---|---|
| 11,642,445 | B2 * | 5/2023 | Laubscher ........ | A61M 16/0003 128/204.23 |
| 2002/0169385 | A1 | 11/2002 | Heinonen et al. | |
| 2012/0103333 | A1 * | 5/2012 | Dingley ............ | A61M 16/0081 128/205.13 |
| 2013/0190582 | A1 * | 7/2013 | Holmstrom ........ | A61B 5/14503 600/364 |
| 2015/0034082 | A1 * | 2/2015 | Kimm ............... | A61M 16/0051 128/202.16 |
| 2016/0150997 | A1 | 6/2016 | Colman et al. | |

FOREIGN PATENT DOCUMENTS

| | | | |
|---|---|---|---|
| WO | 2011021978 | A1 | 2/2011 |
| WO | 2015185618 | A1 | 12/2015 |
| WO | 2016177477 | A1 | 11/2016 |
| WO | 2018106164 | A1 | 6/2018 |

* cited by examiner

22

PROCESS FOR SUPPORTING BLOOD GAS EXCHANGE BY VENTILATION AND EXTRACORPOREAL BLOOD GAS EXCHANGE AND SYSTEM OPERATING ACCORDING TO THE PROCESS

CROSS REFERENCE TO RELATED APPLICATIONS

This application is a United States National Phase Application of International Application PCT/EP2019/063442, filed May 24, 2019, and claims the benefit of priority under 35 U.S.C. § 119 of German Application 10 2018 005 228.2, filed Jul. 3, 2020, the entire contents of which are incorporated herein by reference.

TECHNICAL FIELD

The present invention pertains to a system for supporting the blood gas exchange by means of ventilation and extracorporeal blood gas exchange.

TECHNICAL BACKGROUND

As soon as a patient ceases to be able to breathe spontaneously, he is given technical assistance in order to make possible the exchange of oxygen ($O_2$) and carbon dioxide ($CO_2$) with the cells of the body. The patient's lungs are supported now by different forms of mechanical-pneumatic breathing aids (ventilator) and/or the blood is enriched with oxygen by extracorporeal blood gas exchange (extracorporeal membrane oxygenation) by means of membranes and carbon dioxide is removed.

The degree of invasiveness of the two assistance measures may be different. Gas concentrations, pressures and volumes are the parameters that can be controlled during ventilation by means of a ventilator, and this entails the need for different accesses to the lungs. For example, ventilation without intubation (non-invasive ventilation; NIV) is only possible up to a certain pressure.

Extracorporeal membrane oxygenation (ECMO; other name: Extracorporeal Life Support=ECLS) is known from so-called heart-lung machines (HLM).

Extracorporeal membrane carbon dioxide removal devices ($ECCO_2R$) optimized with respect to $CO_2$ removal and minimal blood flow are available for simultaneous use together with a ventilation by means of a ventilator.

They are distinguished according to blood flow rates, which then require correspondingly dimensioned bloody accesses; for example, a venovenous exchange (without arterial access) is only possible up to an extracorporeal blood flow of up to a maximum of 700 mL/minute.

A portable gas removal device is described in EP 3 291 854 A1. The portable gas removal device has sections for gas removal, a mixing chamber, optional particle filters and controlled pumps for delivering fluids, such as blood and oxygen-containing gas mixtures.

Since the risk of complications increases with increasing degree of invasiveness, it is useful to combine the two processes such that the particular invasiveness is low and the overall risk of complications is thus also as low as possible.

An especially useful example for the combination of ventilation by means of a ventilator and extracorporeal membrane oxygenation by means of carbon dioxide removal devices is the treatment of patients with COPD (chronic obstructive pulmonary disease).

The access to the lungs is narrowed in these patients. A sufficient oxygen ($O_2$) supply can still be ensured adequately in these patients by the administration of an increased $O_2$ concentration. However, high minute volumes are necessary during the ventilation in order to remove carbon dioxide ($CO_2$) via the lungs alone to the necessary extent. As a consequence of the high pneumatic resistance, this requires a high ventilation pressure. To ensure the removal of $CO_2$, it is then necessary to change over from mask ventilation to an invasive ventilation with a tube or tracheotomy. However, avoiding an invasive ventilation has a high priority because of the risks of complications associated therewith precisely in COPD patients.

The ventilation-supporting extracorporeal membrane oxygenation by means of carbon dioxide removal devices has evolved increasingly as a possibility of avoiding the changeover to invasive ventilation, especially the venovenous form with low blood flow.

Coordination of all parameter settings is necessary for a gentle and expedient control and regulation for the overall wellbeing of the patient in case of the simultaneous use of mask ventilation and carbon dioxide removal devices ($ECCO_2R$). This is carried out currently rather according to subjective empirical values. This is prone to errors. In addition, the carrying out of comparable studies and the development of evidence-based therapy guidelines are made difficult.

SUMMARY

An object of the present invention is to propose a possibility for controlling and regulating CO2 and O2 exchange for patients with noninvasive ventilation of the lungs and extracorporeal blood gas exchange possibly on the basis of reproducible and comparable, physiologically relevant measured values.

The key goal of the $CO_2$ removal is an arterial $CO_2$ partial pressure that leads to a quiet, defined respiratory drive (spontaneous breathing; pressure assist by ventilator, ventilator triggered by spontaneous breathing), i.e., neither hyperventilation nor hypoventilation. While this is a defined target range of about 40-45 mmHg in most patients, the endogenous sensor system is already adapted in COPD patients to an increased partial pressure to such a degree that the target range may individually reach up to 65 mmHg. A carbon dioxide removal device is intended for this according to the present invention. Systems for extracorporeal membrane oxygenation (ECMO) or so-called heart-lung machines (HLM), in which the gas exchange takes place outside the human body, and a certain quantity of oxygen is fed to the blood of a patient by means of a membrane and carbon dioxide is removed from the blood of the patient by means of the membrane, can be used as carbon dioxide removal devices in the sense of the present invention.

It is already problematic to provide objective, continuous measured values that are necessary for this for at least individual relevant transport parameters, because suitable measurement methods are not known for all parameters. Especially the following parameters are taken into consideration as transport parameters:

| | |
|---|---|
| $CaO_2$ | arterial $O_2$ content |
| $CvO_2$ | venous $O_2$ content |
| $CaCO_2$ | arterial $CO_2$ content |
| $CvCO_2$ | venous $CO_2$ content |
| $DO_2$ | $O_2$ delivery |

-continued

| | | |
|---|---|---|
| $VO_2$ | $Q \times (CaO_2 - CvO_2)$ | $O_2$ uptake |
| $VCO_2$ | $Q \times (CvCO_2 - CaCO_2)$ | $CO_2$ elimination |
| RQ | $VCO_2/VO_2$) | respiratory quotient |

It is also impossible to determine with sufficient accuracy an objective continuous measured value for the $CO_2$ content in the blood on the basis of a $CO_2$ concentration measured value obtained by measurement in the breathing gas during mask ventilation despite optimal adaptation of the measuring set-up.

Estimation methods, which are subject to errors, have rather been hitherto necessary to obtain an approximate value for the $CO_2$ content in the blood. In addition, the therapeutically desirable target value of the $CO_2$ content of the blood for COPD patients is increased compared to normal patients and is subject to great individual variations. Such a target value cannot therefore be determined for a therapist in a simple manner, nor can it be read from a guideline.

The innovation being presented here is based on the principle of determining a trend parameter, especially a unitless trend parameter, for the $CO_2$ content in the blood as well as of the use of such a trend parameter for an objectively comparable and reproducible checking process for the $CO_2$ partial pressure of the blood ($PaCO_2$), doing so on the basis of a stable state determined by a physician.

The expiratory $CO_2$ concentration determined by measurement in the breathing gas of the patient is often also available as an expiratory $CO_2$ concentration measured value, which is detected towards the end of the exhalation as a so-called end-expiratory $CO_2$ concentration in the breathing gas of the patient, often also called end-tidal carbon dioxide concentration ($etCO_2$). The end-tidal carbon dioxide concentration ($etCO_2$) is sufficiently significant in many cases for the diagnosis concerning the conversion of oxygen into carbon dioxide in the metabolism, but the time curve of the expiratory $CO_2$ concentration or representative values from this time curve may show additional information on the gas exchange and metabolism.

Consequently, the expiratory $CO_2$ parameters and expiratory $CO_2$ measured values as well as the end-expiratory $CO_2$ parameters and end-expiratory $CO_2$ measured values will be explained in the sense of the following invention as a special embodiment or subset of the expiratory $CO_2$ parameters and expiratory $CO_2$ measured values in the description together and used next to each other by means of symbols, abbreviations, reference numbers and formulas, for example, in the form ($CO_2$; $etCO_2$).

In the ideal case in terms of measurement, a $CO_2$ sensor located, for example, in a breathing mask detects the $CO_2$ content in the alveolar air in the lungs towards the end of the exhalation. Due to the physiology, the $CO_2$ partial pressure ($pCO_2$), especially the end-tidal $CO_2$ partial pressure ($PetCO_2$) at the end of the exhalation is almost in equilibrium with the arterial $CO_2$ partial pressure of the arterial blood ($PaCO_2$) of a patient.

In the most unfavorable case in terms of measurement, only a mean $CO_2$ value, which hardly differs between inhalation and exhalation, is detected by means of the $CO_2$ sensor. This may be due to the location of the measurement in the mask, at which mixing of inhaled and exhaled gases takes place. Even in this case, there is a physiological relationship between the $CO_2$ concentrations measured during exhalation and at the end of the exhalation ($CO_2$; $etCO_2$), the $CO_2$ partial pressure ($PCO_2$; $PetCO_2$) and the arterial $CO_2$ partial pressure of the arterial blood ($PaCO_2$). However, the measured value is influenced by factors such as, for example, the breathing pattern (I:E ratio) and a leakage of the mask (influencing factors). As long as these influencing factors do not change in the course of the ventilation or the treatment of the patient, this relationship is preserved, as it were, as a correlation. This relation is also valid in a comparable manner if the values referred to are obtained at approximately the same times during the exhalation, likewise under the boundary condition that these influencing factors do not change in the course of time of ventilation or the treatment of the patient and the times at which the data are determined and the data are acquired do not change during the exhalation in the course of time during the ventilation or the treatment of the patient.

The expiratory $CO_2$ concentration (measured value) or the end-expiratory $CO_2$ concentration (measured value), which are detected by measurement by means of a sensor system, for example, a sensor system in a breathing mask, will hereinafter be called $CO_2$mess and $etCO_2$mess, respectively. This depends, as is shown, individually on the patient as well as on the ventilation situation. Optimization of the $CO_2$ measurement is desired during mask ventilation, during which the detected measured value ($CO_2$mess; $etCO_2$mess) depends as little as possible on the influencing factors, so that the correlation with $PaCO_2$ is preserved even in case of changes in the influencing factors. Provisions are made for this purpose for assuming as the starting value a measured value recorded as being acceptable ("snapshot") and, on the other hand, for standardizing measured values that follow in time in reference to the start value. The setting of a start value, i.e., the selection of a measured value as an acceptable value, is carried out by medically trained staff, especially a physician.

The trend parameter called $CO_2$equal and $etCO_2$equal below is obtained as a unitless quotient (unitless trend parameter) from a respective current measured value $CO_2$mess(k) and $etCO_2$mess(k), respectively, and the set start value, wherein the start value is the measured value $CO_2$mess(k=0) and $etCO_2$mess(k=0) recorded at a start time (k=0):

$$CO_2\text{equal} = CO_2\text{mess}(k)/CO_2\text{mess}(0) \text{ and}$$

$$etCO_2\text{equal} = etCO_2\text{mess}(k)/etCO_2\text{mess}(0).$$

At the time k=0, this quotient is preferably standardized to 1.0; as an alternative, the standardization may also be carried out to 100%. The value of 1.0 and 100% are thus obtained for the trend parameter $CO_2$equal and $etCO_2$equal for the time k=0. In the further course of the ventilation, the trend parameter then fluctuates around 1.0 and around 100%. The desired independence of the resulting trend parameter $CO_2$equal and $etCO_2$equal from possible changes in the influencing factors is obtained in this manner by means of the initial determination of an acceptable start value and the later quotient formation. The acceptable start value can be defined, for example, on the basis of an evaluation of a clinical user or it may be obtained from tables with evaluations and assignments of the quotient to certain patient states.

The trend parameter may be used as a controlled variable (actual value) of a regulation. Based on the standardization of the trend parameter, the value 1.0 or 100% can be used as the set point (command variable). The trend parameter is sought to be kept constant by means of the regulation. By means of resulting manipulated variables, the regulation influences, for example, a delivery device of the $CO_2$ removal device ($ECCO_2R$) and/or a fan of the $CO_2$ removal device. A manipulated variable influencing the delivery device influences the quantity of blood flowing through the $CO_2$ removal device (blood flow rate). A manipulated variable influencing the fan influences the gas exchange in the blood within the $CO_2$ removal device. An exemplary embodiment of the regulation is explained in the special description part. Based on the principle of a regulation on the basis of a trend parameter, it was found that an even more simple form of a regulation is possible by attempting to express it concisely by means of the regulation to maintain an expiratory or end-expiratory $CO_2$ concentration set as an acceptable concentration in the breathing gas at a constant value or to maintain it at least essentially at a constant value.

The above-mentioned object is thus accomplished according to the present invention by means of a system as well as by means of a process.

Provisions are made to this end in such a system for supporting the blood gas exchange of a patient by means of ventilation, on the one hand, as well as by means of extracorporeal blood gas exchange by means of a $CO_2$ removal device, on the other hand, as well as by means of a process for operating such a system

- for a measured value ($CO_2$mess; $etCO_2$mess) concerning an expiratory $CO_2$ concentration (carbon dioxide concentration) to be able to be detected in the breathing gas of the patient and to be detected during the operation of the system by means of a sensor system, especially by means of a sensor system comprised by the system or associated with the system,
- for a current measured value concerning the expiratory or end-expiratory $CO_2$ concentration in the breathing gas ($CO_2$mess(0); $etCO_2$mess(0)) to be able to be selected as a start value by means of an operating action, especially by an operating action on an input device of a device comprised by the system,
- and for the start value to act as the basis for a regulation by means of a controller,
- wherein the controller acts on a $CO_2$ removal device, i.e., for example, a manipulated variable outputted by the controller acts as a set point for the $CO_2$ removal device.

In a preferred embodiment, a measured value concerning an end-expiratory $CO_2$ concentration ($etCO_2$) in the breathing gas of the patient can be detected by means of the sensor system as a measured value concerning the expiratory $CO_2$ concentration ($etCO_2$) in the breathing gas of the patient. The selection of the end-expiratory $CO_2$ concentration ($etCO_2$), often also called end-tidal carbon dioxide concentration ($etCO_2$), makes it possible to detect measured values at times recurring in the rhythm of the breathing in a defined manner in approximately identical states of the patient, and these measured values are then used both as an input variable that is steadily updated in the course of time of the therapy and ventilation for the controller and also at the beginning of the therapy when the start value is determined. If end-expiratory $CO_2$ concentration measured values ($etCO_2$) are used as expiratory $CO_2$ concentration measured values in the breathing gas of the patient, synchronization of the measurement sampling is obtained for the regulation in analogy to the ventilation control, so that changes can be made by the user during the operation in the ventilation control, e.g., in the ventilation frequency, without the measurement sampling additionally requiring an adjustment, because the $CO_2$ measured value is obtained independently from the change in the setting at the end of the exhalation. This leads to the advantage of achieving robustness in the measured value acquisition and hence indirectly also in the regulation according to the present invention with an effect on the $CO_2$ removal device compared to configurations of other embodiments. In addition, solutions with $CO_2$ removal device can be configured in practice, whose regulation can also be made possible according to the present invention without data information from a ventilator or of a ventilation control by means of the manipulated variable outputted by the controller as a set point for the $CO_2$ removal device.

In other embodiments, measured values can be detected by the sensor system at any desired times, which are, however, defined in the time course of the ventilation, during the exhalation. The position in time of the measured value acquisition within the exhalation phase is to be defined suitably in such embodiments on the basis of events of the ventilation process or on the basis of times and is then to be adapted to respective ventilation settings (RR, I:E), adapted by means of a time control coordinated for the ventilation control with ventilation rate (RR) and inhalation to exhalation ratio (I:E ratio).

The data acquisition necessary for the regulation, namely expiratory $CO_2$ concentrations in the breathing gas towards—especially also exactly at—the end ($etCO_2$) of the exhalation offers, moreover, the advantage that the flow conditions at the measuring site (e.g., Y-piece) of the detection of the $CO_2$ concentration in the breathing gas at these times also remain comparatively stable during a longer time course of the ventilation or treatment of the patient, so that the changes in the end-expiratory $CO_2$ concentrations used to regulate the $CO_2$ absorber in the course of the ventilation or treatment of the patient are not caused essentially by flow effects or no flow effects are superimposed to them.

The function of the start value as the basis for the regulation can be in two forms:

1. On the one hand, the start value can act as the basis for a regulation, by a difference from the start value and a respective current measured value can be fed to the controller acting on the $CO_2$ removal device and is fed to the controller during the operation of the system.
2. On the other hand, the start value can act as a basis for a regulation by a difference from a trend parameter formed with the start value and a set point for the trend parameter can be fed to the controller acting on the $CO_2$ removal device and is fed to the controller during the operation of the system.

Provisions are optionally made in a regulation on the basis of the difference between the trend parameter formed by the set point and the set point for the trend parameter for the trend parameter ($CO_2$equal; $etCO_2$equal) to be able to be determined with the start value ($CO_2$mess(0); $etCO_2$mess (0)), on the one hand, as well as with a respective, currently determined measured value ($CO_2$mess(k); $etCO_2$mess(k)), on the other hand, namely, with a measured value concerning the expiratory or end-expiratory $CO_2$ concentration in the breathing gas, for example, in the form of the quotient formation mentioned, and it is determined during the operation of the system within the framework of the process. As an alternative to the quotient formation, it is also possible to select a, for example, weighted difference formation to determine the trend parameter ($CO_2$equal; $etCO_2$equal). A difference between the set point for the trend parameter, for example, 1.0 or 100%, as well as a respective current value of the trend parameter can be fed to a controller and is fed to the controller, the controller acting on the $CO_2$ removal device, i.e., for example, a manipulated variable outputted by the controller acts as a set point for the $CO_2$ removal device.

Based on the fact that the control system, i.e., the gas content of the blood of the patient, is equal in both situations (regulation on the basis of a measured value recorded as a start value as well as of a current measured value or regulation on the basis of the trend parameter), it is assumed that the quality of the two regulation possibilities is equal or at least essentially equal.

Stabilization of the expiratory or end-expiratory $CO_2$ concentration originally recorded as acceptable in the breathing gas (start value) or stabilization of the trend parameter is sought to be achieved by means of the regulation. The regulation is thus also called, as a whole, preservation regulation. In case of a regulation with reference to the trend parameter, which is referred to the start value due to it being formed with the start value, on the one hand, and with a respective, currently detected measured value, on the other hand, it is achieved with the stabilization of the trend parameter that the expiratory or end-expiratory $CO_2$ concentration in the breathing gas of the patient, which concentration is included in the trend parameter in the form of the measured value, remains at least in the range around the start value. The start value is selected as a start value because this was evaluated by an operator of the system, usually a physician, as being acceptable. It is thus achieved by means of the regulation that the expiratory or end-expiratory $CO_2$ concentration in the breathing gas of the patient remains at least in the range around a value medically considered to be acceptable.

The above-mentioned object is likewise accomplished by the use of a system of the type here and hereinafter described. A measured value is detected and optionally displayed as an indicator of an expiratory or end-expiratory $CO_2$ concentration in the breathing gas of the patient by means of the system and a sensor system comprised by the system or associated with the system. The presence of an acceptable $CO_2$ concentration in the breathing gas is confirmed by an operator of the system by an operating action. Such an operating action is followed within the framework of an operation of the system by a regulated operation of the $CO_2$ removal device comprised by the system with the goal of maintaining the $CO_2$ concentration characterized as being acceptable. Carbon dioxide is removed from the blood of the patient during the regulated operation of the $CO_2$ removal device. The regulated operation of the $CO_2$ removal device can take place in the form of a stabilization of the $CO_2$ concentration originally selected as being acceptable, which stabilization is brought about or at least sought to be achieved by the regulation, or in the form of a stabilization of a trend parameter formed with the $CO_2$ concentration originally selected as being acceptable.

The process for operating the system and embodiments of the process, which will be described below, as well as the process steps comprised by said process are carried out automatically, i.e., without a special involvement of the user of the system. The automatic performance of the process steps is carried out under the control of a control unit. This comprises a processing unit in the form of or in the manner of a microprocessor as well as a memory. A control program, which is executable by the processing unit and which is executed during the operation of the system by the processing unit, is loaded or can be loaded into the memory.

The above-mentioned object is thus also accomplished by means of a control unit, which operates according to the process as here and hereinafter described and comprises means for carrying out the process to this end. The present invention is preferably implemented in software. The present invention is thus also a computer program with program instructions executable by a computer, on the one hand, and a storage medium with such a computer program, i.e., a computer program product with program code means, on the other hand, and finally also a control unit or a medical device, in the memory of which control unit or medical device such a computer program is loaded or can be loaded as a means for carrying out the process and configurations thereof.

One advantage of the present invention is that an objectively comparable and reproducible checking process is proposed for the $CO_2$ partial pressure of the blood ($PaCO_2$), starting from a medically determined stable state, and the measured value recorded for this as a start value concerning the expiratory or end-expiratory $CO_2$ concentration in the breathing gas. The process still ensures an optimal or at least acceptable $CO_2$ partial pressure in the blood even in case of insufficient $etCO_2$ measurement based on leakages from the mask.

References used here refer to the further configuration of the subject of the principal claim by the features of the respective subclaim and they shall not be considered to represent abandonment of achieving an independent concrete protection for the combinations of the features of the referred subclaims. Furthermore, it shall be assumed in respect to an interpretation of the claims as well as of the description in case of a more specific concretization of a feature in a dependent claim that such a limitation is not present in the respective preceding claims as well as in a more general embodiment of the concrete system or process. Any reference in the description to aspects of dependent claims shall accordingly also expressly imply a description of optional features even without a special reference. Finally, it should be noted that the system being proposed here may also be perfected corresponding to the dependent process claims and vice versa, for example, by the system comprising means that are intended and/or set up for carrying out one or more process steps or by the process comprising steps that can be carried out by means of the system. Thus, features and details that are described in connection with the system being proposed for supporting the blood gas exchange by means of ventilation as well as extracorporeal blood gas exchange and in connection with possible embodiments are also valid in connection with and in respect to a process carried out during the operation of the system and vice versa, so that reference is and can always mutually be made to the individual aspects of the present invention concerning the disclosure.

In one embodiment of the system or of the process, the trend parameter ($etCO_2$equal) can be determined in the form of a standardization of the respective, currently determined measured value ($etCO_2$mess(k)) in relation to the start value ($etCO_2$mess(0)) and is determined by means of such a standardization as a unitless trend parameter, for example, by quotient formation:

$$etCO_2\text{equal} = etCO_2\text{mess}(k)/etCO_2\text{mess}(0).$$

In another embodiment of the system or of the process, the respective current measured value can be outputted with respect to the expiratory or end-expiratory $CO_2$ concentration in the breathing gas at a display unit and it is outputted during the operation of the system at the display unit.

The displayed measured value can be selected as a start value by means of the operating action and it is selected as a start value during the operation of the system. Without such a display unit, i.e., in the hitherto described form of the system and process, the operator of the system, i.e., usually a physician, performs the operating action selecting the start value on the basis of an observation of the patient. The aim of the observation is to detect a stable breathing behavior of the patient (quiet, defined respiratory drive). With such a display unit, the operator of the system can take into consideration the observed breathing behavior of the patient, on the one hand, and the respective displayed measured value, on the other hand, and then determine the time for his operating action, which triggers the recording of the start value and subsequently the preservation regulation.

A spontaneous respiratory rate of the patient can be monitored by means of a sensor system in a preferred embodiment of the system or of the process and it is monitored within the framework of the process, and if a predefined or predefinable threshold value is exceeded, a signal element can be actuated and is actuated within the framework of the process in such a case in which a threshold value is exceeded.

In a preferred embodiment of the system or of the process, a weaning mode can be activated by means of an operating action and it is activated by an operating action of the operator during the operation of the system in case of a corresponding decision made by an operator of the system, wherein a desired $CO_2$ removal target can be reduced automatically and in a controlled manner in the weaning mode and it is reduced within the framework of the process.

In a special embodiment of the aforementioned advantageous embodiment of the system, the preservation regulation can be deactivated at or in connection with the beginning of the reduction of the $CO_2$ removal target, for example, by the influence of the controller on the $CO_2$ removal device being able to be deactivated. However, the trend parameter nevertheless continues to be determined. This parameter can be monitored during the reduction of the $CO_2$ removal target in reference to a predefined or predefinable tolerance range. When moving out of the tolerance range, the preservation regulation can be reactivated, on the one hand, for example, by the influence of the controller on the $CO_2$ removal device being reactivated, and, on the other hand, the current reduction of the $CO_2$ removal target can be deactivated. The preservation regulation is deactivated in a corresponding process during or in connection with the beginning of the reduction of the $CO_2$ removal target. The trend parameter, which continues to be determined, is monitored during the reduction of the $CO_2$ removal target in reference to a predefined or predefinable tolerance range. In case of moving out of the tolerance range, the preservation regulation is reactivated, on the one hand, and the current reduction of the $CO_2$ removal target is deactivated, on the other hand.

An automatic and automatically monitored weaning of the patient from the effect of the $CO_2$ removal device is possible with this embodiment of the system or of the process provided for operating the system. The weaning is in the form of a reduction of the $CO_2$ removal target. Due to the determination of the trend parameter, which is also carried out during the weaning, the course of the weaning can be monitored. If the trend parameter leaves a tolerance range, the reduction of the $CO_2$ removal target is stopped and the preservation regulation is activated. If a permissible and/or stable trend parameter becomes established again within the framework of the preservation regulation, the preservation regulation can be stopped again and the reduction of the $CO_2$ removal target can start again. When the tolerance range is moved out of here again, the preservation regulation is reactivated, etc. This automatic weaning of the patient may be carried out until a target value is reached concerning the $CO_2$ removal target.

An exemplary embodiment of the present invention will be explained in more detail below on the basis of the drawings. Mutually corresponding objects or elements are provided with the same reference numbers in all figures.

The exemplary embodiment shall not be considered to represent a limitation of the present invention. Rather, variations and modifications, especially such variants and combinations which the person skilled in the art can find in respect to accomplishing the object, for example, by a combination or variation of individual features contained in the general or special text of the description as well in the claims and/or in the drawings and lead to a new subject by combinable features, are possible within the framework of the present disclosure.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
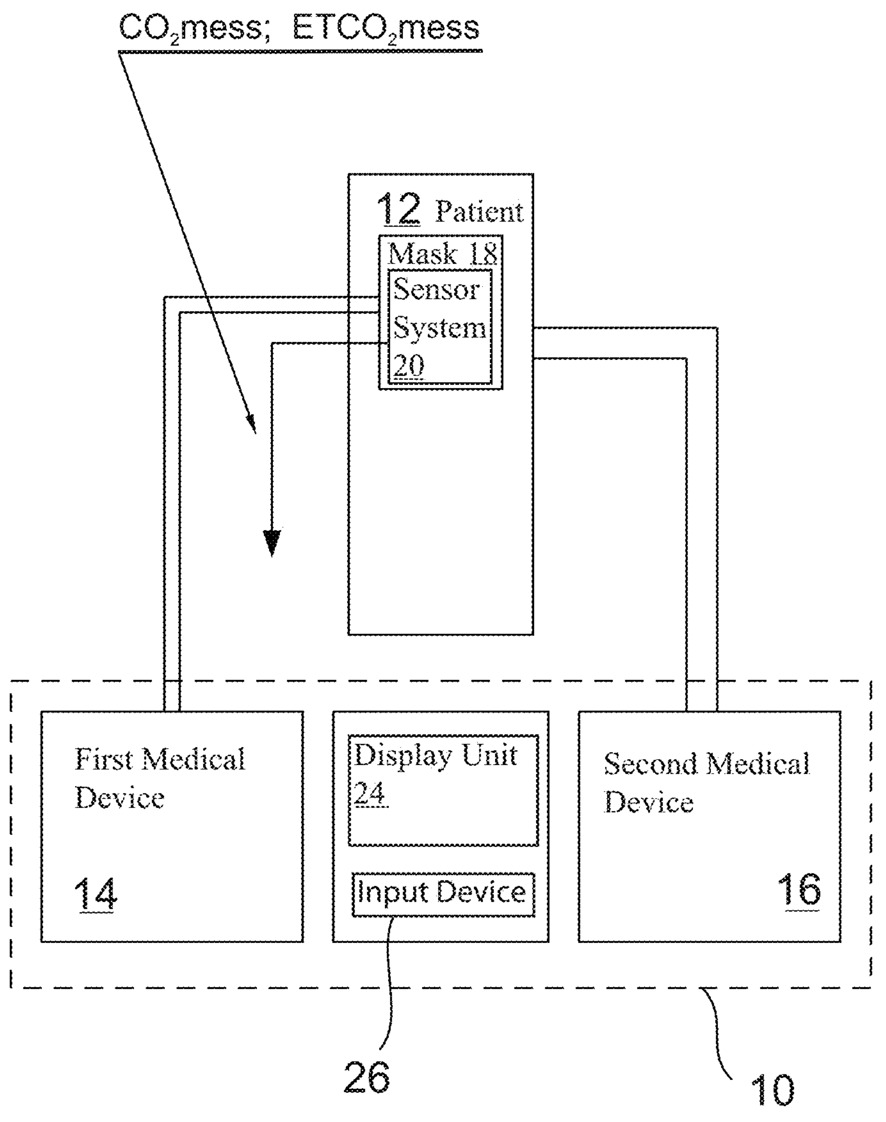
FIG. 1 is a schematic view of a system for ventilating a patient, which comprises at least one medical device acting as a ventilator.

Referring to the drawings, the view in FIG. 1 shows, in a highly simplified, schematic form, a system 10 for supporting a gas exchange in a patient 12. The system 10 comprises at least two medical devices 14, 16, namely, a first medical device 14 in the form of a ventilator for the mechanical ventilation of the lungs of the patient 12 and a second medical device 16 for extracorporeal blood gas exchange. At least a removal of carbon dioxide ($CO_2$) from the blood of the patient 12 and possibly an enrichment of the blood with oxygen ($O_2$) are carried out by means of the second medical device 16. The first medical device 14 acting as a ventilator will hereinafter be called, for short, but without abandoning a further general validity, a ventilator 14. The second medical device 16 intended at least for the removal of carbon dioxide from the blood of the patient 12 will correspondingly be called for short, likewise without abandoning a further general validity, a $CO_2$ removal device 16. Devices 14, 16 of the above-mentioned type are known per se. A $CO_2$ removal device 16 is also called at times $ECCO_2R$ for short in the technical literature.

The ventilator 14 is connected in the manner known per se non-invasively to the lungs of the patient 12, for example, by means of a breathing mask 18. The $CO_2$ removal device 16 is likewise connected in the manner known per se to the blood circulation of the patient 12.

A measured value concerning an expiratory or end-expiratory $CO_2$ concentration in the breathing gas of the patient can be detected by means of a sensor system 20 comprising at least a $CO_2$ sensor, for example, a sensor system 20 located in the breathing mask 18 in the manner known per se, during the operation of the ventilator 14 and, on the whole, during the operation of the system 10. This measured value will hereinafter be called at times $etCO_2$mess for short.

One of the at least two medical devices 14, 16, for example, the ventilator 14, acts within the system 10 as a higher-level device or the system 10 comprises a dedicated higher-level device or an additional medical device 22 acting as a higher-level device and as a control unit. The following description will be continued on the basis of a system 10 with such an additional medical device 22 and this is called a control device 22. It is just as well considered, in principle, that the system 10 does not comprise any such additional medical device 22 and that the ventilator 14 or even the $CO_2$ removal device 16 acts instead as a control unit. This shall always be implied in the following whenever a higher-level device or a control unit is mentioned. In case of a separate control unit 22, this is connected communicatively in the manner known, in principle, per se to the other devices 14, 16 of the system 10 at least for the exchange of data, especially in the form of measured values and/or control signals. In the case of a system 10 without such a separate control unit, the device 14, 16 acting as a control unit is connected to the other devices 14, 16 of the system in the manner outlined above.

The device acting as a control unit 22 comprises in the embodiment shown a display unit 24 as well as an input device 26 or is connected to a device or devices with a display unit 24 and/or with an input device 26 in the manner known, in principle, per se. The measured value ($etCO_2$mess) that can be regularly recorded by means of the sensor system 20 and is regularly recorded during the operation of the system 10 is outputted to the system 10 and is processed within the system 10. A display unit 24 is optional. The output of the measured value is carried out directly or indirectly to the device acting as a control unit 22 and the processing of the measured value comprises, in case of an existing display unit 24, at least a display of the measured value by means of the display unit 24. The display of the measured value by means of the display unit 24 makes it possible for an operator of the system 10, usually a physician, to monitor the measured value. Without such a display of the measured value, the operator evaluates the patient 12 himself, i.e., for example, his breathing behavior. When the operator finds a satisfactory breathing behavior of the patient 12 and/or a measured value in an acceptable range or a measured value that remains stable over a sufficiently long time period in an acceptable range, which measured value is outputted by means of the display unit 24, he carries out an operating action on the system 10. It is expressed by means of the operating action that a satisfactory breathing behavior and/or an acceptable displayed measured value are present. In case of a satisfactory breathing behavior as the only criterion for performing the operating action, it can be assumed that the measured value ($etCO_2$mess) recorded by means of the sensor system 20—independently from a possible display by means of the display unit 24—is likewise an acceptable measured value or a measured value in an acceptable range. The recorded, current and optionally displayed measured value can be selected as a start value for a reproducible extracorporeal $CO_2$ removal by means of the $CO_2$ removal device 16, which takes place according to the principle being proposed here by means of the operating action, for example, an operating action in the form of an actuation of the input device 26.

Figure 2:
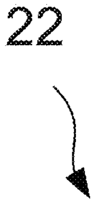
FIG. 2 is a schematic view of a device acting as a control unit in the system according to FIG. 1.
Figure 2:
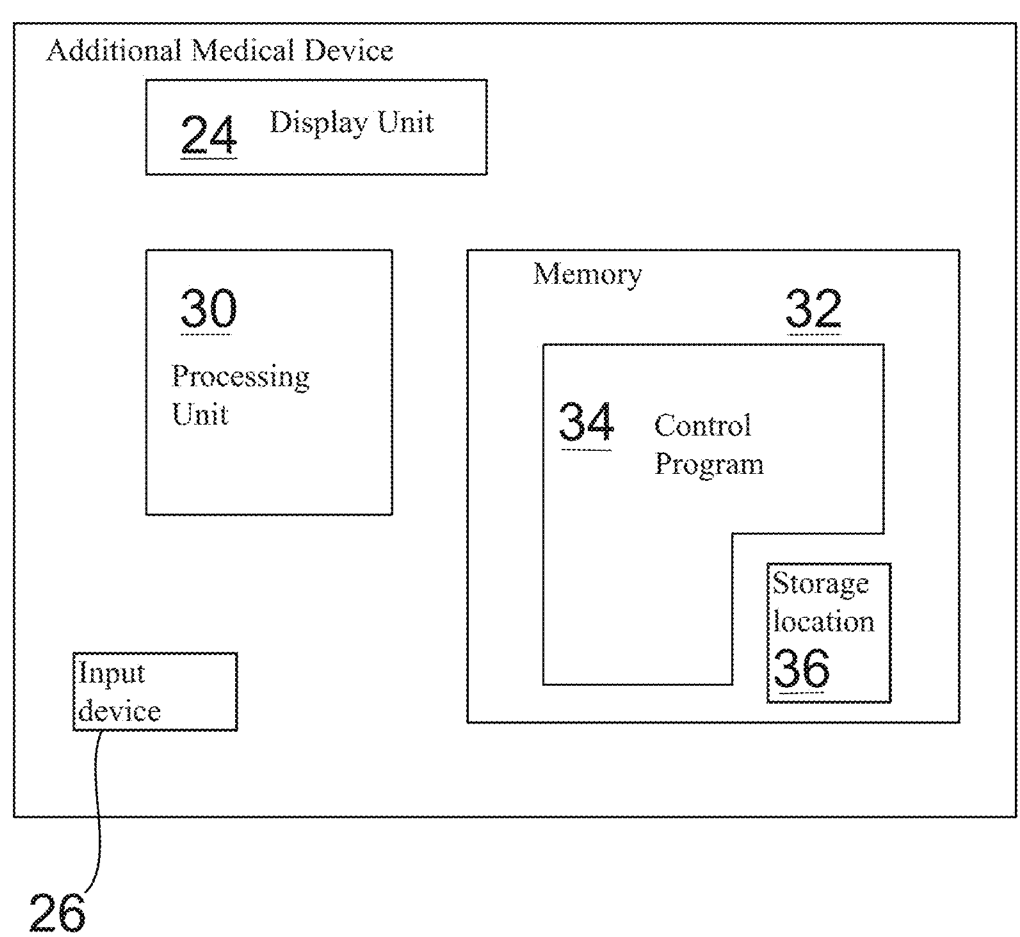

The view in FIG. 2 shows—likewise in a schematically highly simplified manner—the device acting as a control unit 22 in the system 10 (FIG. 1), i.e., for example, the additional medical device 22, where the additional medical device 22 may be, for example, a medical device in the form of a therapy device or the like, which is associated with or is hierarchically at a higher level than the ventilator 14 and the $CO_2$ removal device 16. The control unit 22 comprises the (optional) display unit 24 and the input device 26. These may be each elements of a user interface represented by means of a monitor of the control unit 22 in a manner known basically per se. The control unit 22 comprises, furthermore, a processing unit 30 in the form of or in the manner of a microprocessor as well as a memory 32, into which a control program 34 is loaded, which is executed by means of the processing unit 30 during the operation of the control unit 22. For example, the display of the user interface and the analysis of operating actions, which pertain to the user interface, if the control unit 22 uses such a user interface, also take place under the control of the control program 34. At any rate, the actuation of the display unit 24 and hence the display of the measured values and the analysis of the input device 26 for detecting possible operating actions also take place under the control of the control program 34.

If a measured value recorded by means of the sensor system 20 was selected as an acceptable measured value by such an operating action, either based on an observation of the patient 12 or on the basis of an observation of the display unit 24, this measured value is recorded as a start value, for example, in a start value storage location 36 in the memory 32 and is loaded to this end into the start value storage location 36.

Figure 3:
FIG. 3 is a schematic view of a control circuit for regulating the extracorporeal blood gas exchange of a patient.
Figure 3:
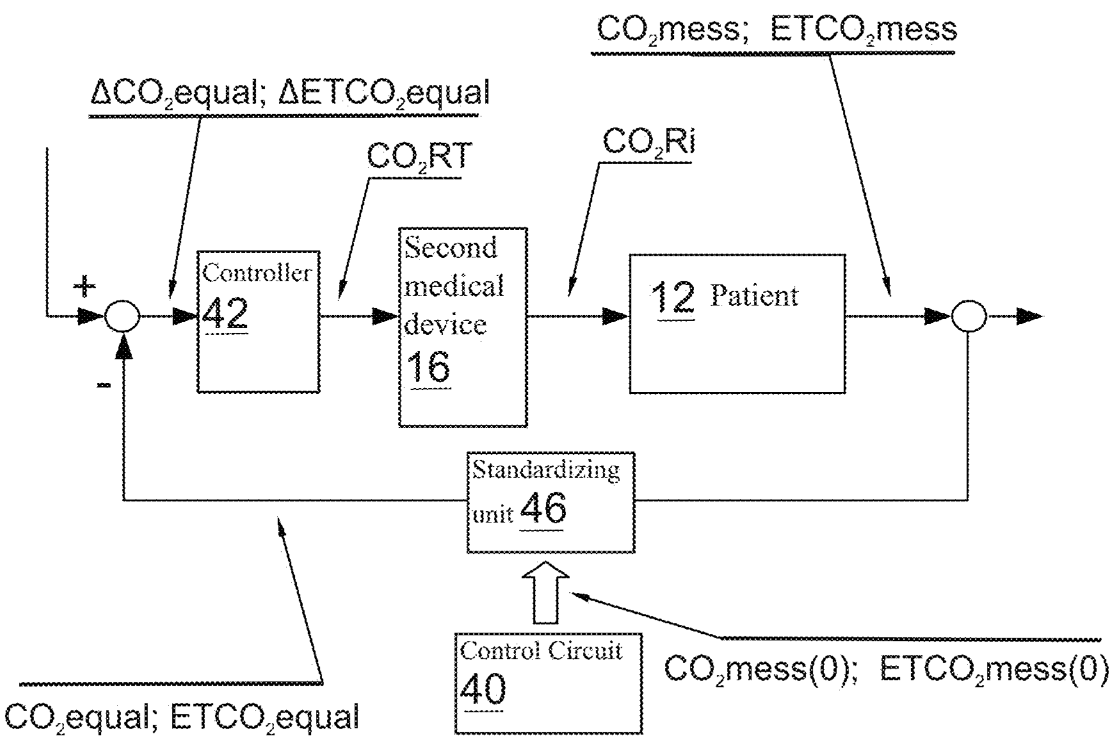

The view in FIG. 3 shows a control circuit 40 for the implementation of the regulation explained in the general part of the description for stabilizing a trend parameter, which is based on a respective, currently determined measured value (preservation regulation). The following description correspondingly applies to a regulation for stabilizing the start value, and a regulation, whose goal is to stabilize the start value instead of a stabilization of the trend parameter, shall always be implied.

The control circuit 40 comprises, in the manner known, in principle, per se, a controller 42, for example, a P controller, a PI controller or a PID controller, preferably a PI controller. The controller 42 acts on the $CO_2$ removal device 16 and the control system is formed by the $CO_2$ removal device 16 and by the patient 12. The $CO_2$ removal device 16 acts on the patient 12 with a $CO_2$ removal rate ($CO_2$Ri). The $CO_2$ removal device 16 is actuated in the manner known per se with a $CO_2$ removal target ($CO_2$Rt) acting as a set point for the $CO_2$ removal. The $CO_2$ removal device 16 is actuated within the control circuit 40 by the controller 42. The controller 42 consequently predefines the $CO_2$ removal target as the manipulated variable.

The measured value determined in the control circuit 40, namely at the patient 12, is the measured value concerning the expiratory or end-expiratory $CO_2$ concentration ($etCO_2$mess), which is determined in the breathing gas exhaled by the patient by means of a sensor system 20 (FIG. 1) known, in principle, per se. The measured value is standardized in the return branch of the control circuit 40 with a measured start value 44 ($etCO_2mess(0)$) determined prior to the activation of the regulation and polled, for example, from the start value storage location 36 to obtain a trend parameter ($etCO_2equal$). This is carried out by means of a standardizing unit 46. The standardization by means of the standardizing unit 46 comprises the quotient formation explained in the general part of the description. The trend parameter is determined now with the respective current measured value concerning the expiratory or end-expiratory $CO_2$ concentration ($etCO_2mess(k)$) and the start value 44. For example, the value 1.0 or the value 100% acts as a command variable/set point.

The deviation ($\Delta etCO_2equal$) is obtained by subtraction in a manner known, in principle, per se with the command variable and with the trend parameter returned in the return branch. If the trend parameter determined on the basis of the respective detected expiratory or end-expiratory $CO_2$ concentration deviates from the set point, the regulation comes into action by the controller 42 changing the $CO_2$ removal target. The intervention of the controller 42 takes place now by the set point for the $CO_2$ removal rate ($CO_2$ removal target) being increased in case of an increase in the trend parameter. As a result, the $CO_2$ content drops in the blood. This leads to a reduction of the respiratory drive of the patient 12. An increase in the trend parameter is equivalent (because $etCO_2equal=etCO_2mess(k)/etCO_2mess(0)$) to an increased expiratory or end-expiratory $CO_2$ concentration ($etCO_2mess(k)$) in the breathing gas of the patient 12 compared to the start value ($etCO_2mess(0)$).

An optional improvement concerning the detection of an indicator for the expiratory or end-expiratory $CO_2$ concentration in the breathing gas of the patient 12 may be, for example, that an estimated value is determined for $etCO_2mess$ under ideal measurement conditions, i.e., more or less an ideal measured value is obtained, on the basis of information on inspiratory efforts, which may be indicated, for example, by the spontaneous respiratory rate ($f_{spontan}$) and/or by the I:E ratio. This ideal measured value will hereinafter be called $etCO_2ideal$. The information concerning the spontaneous respiratory rate ($f_{spontan}$) and the I:E ratio (I:E) may originate either from an additional sensor system or from a flow sensor integrated into the sensor system 20 (FIG. 1) or directly from the breathing phase detection by the $CO_2$ sensor. Under the assumption that the ventilation of the patient 12 takes place with a negligibly low inspiratory $CO_2$ concentration, the following estimated value is obtained for $etCO_2ideal$ under the assumption of constant inspiratory and expiratory $CO_2$ concentrations:

$$etCO_2\text{ideal} = \text{CO}_2(exsp) + \text{CO}_2(insp) * (I{:}E).$$

The following formula, in which the entire $CO_2$ concentration measured during a breath (T) is added to the exhalation phase (Te), can be used in the general case of $CO_2$ concentrations variable over time, $CO_2(t)$:

$$et\text{CO}_2ideal = \frac{1}{Te}\int_0^T \text{CO}_2(t)dt$$

Here, Te is the duration of the exhalation and T is the duration of the breath, i.e., T=Ti+Te and T=1/f.

In the limit case of a disappearing inspiratory $CO_2$ concentration, this leads, as expected, to:

$$et\text{CO}_2ideal = \frac{1}{Te}\int_0^{Te} \text{CO}_2(t)dt = \text{CO}_2(exsp)$$

In the limit case of equal inspiratory and expiratory concentrations (greatly smoothed measured values), we obtain:

$$et\text{CO}_2ideal = \frac{1}{Te}\int_0^T \text{CO}_2\,dt = \frac{T}{Te}\text{CO}_2 = (1 + I{:}E)\,\text{CO}_2$$

It is assumed in each case that the non-disappearing $CO_2$ concentration during the inhalation represents a measurement artifact, so that a correction of etCOmess to $etCO_2ideal$ is favorable.

The calculation of $etCO_2equal$ is carried out, analogously to the above-described calculation, by standardization to the start value of $etCO_2ideal$, which is categorized as being medically acceptable:

$$et\text{CO}_2equal\,(k) = \frac{et\text{CO}_2ideal(k)}{et\text{CO}_2ideal(k=0)}$$

Independently from the use of $etCO_2mess$ or $etCO_2ideal$, the time k=0 is the "initial time" at which the patient 12 is evaluated by the physician as "o.k." More complicated forms of the calculation of $etCO_2equal$ with the inclusion of the spontaneous respiratory rate as a weighting factor or for case differentiation are likewise possible and useful. The controller 42, the processing of the measured values, the return in the control circuit 40 and the determination of the deviation at the input of the controller 42 are preferably implemented in software. The corresponding details of the view in FIG. 3 thus show a part of the functionality of the control program 34 of the control unit 22. The spontaneous respiratory rate ($f_{spontan}$) of the patient 12 can optionally be monitored by means of a corresponding sensor system (not shown), which is known, in principle, per se. A significant change, i.e., a change in the spontaneous respiratory rate exceeding a predefined or predefinable threshold value (for example, a value exceeding a spontaneous respiratory rate of 30 per minute), during the above-described preservation regulation, may suggest an impairment of the quality of the measurement of the expiratory or end-expiratory $CO_2$ concentration ($etCO_2mess(k)$). The respective measured value is directly included in the determination of the trend parameter and the quality of the measured value thus determines the quality of the preservation regulation. It is therefore optionally proposed that in case of a sensory monitoring of the spontaneous respiratory rate in case of a change in the spontaneous respiratory rate exceeding a predefined or predefinable threshold value, an alarm be automatically triggered, for example, by means of an optical and/or acoustic signal element. Based on such an alarm, the operating staff can check, for example, the fitting of a ventilation mask or the like and correct it if necessary.

In such an optional embodiment, the analysis of a measured value coding the spontaneous respiratory rate and the monitoring of the measured value in reference to the threshold value is preferably likewise implemented as a part of the functionality of the control program 34 of the control unit 22. Taken by itself, the comparison of a measured value with a threshold value and the actuation of a signal element in case a threshold value is exceeded are trivial and corresponding functional elements or program code instructions are not shown here accordingly.

In addition or as an alternative, an automatically supported "weaning" of the patient 12 from the support by the $CO_2$ removal device 16 may be optionally provided. The beginning of such a weaning is activated by the operator of the system 10 (FIG. 1), for example, in the form of an operating action, for example, of an actuation of an input device 26, especially of an additional input device (key, switch, element of a user interface or the like). The system 10 then switches into a weaning mode. The preservation regulation (FIG. 3) is at first deactivated in the weaning mode. The weaning mode is characterized in that the $CO_2$ removal target ($CO_2Rt$) is reduced by a predefined or predefinable value, for example, by 3 mL/minute per hour. The current values of the trend parameter $etCO_2equal$ continue to be determined and monitored continuously in the weaning mode. When the respective current value of the trend parameter moves out of a predefined or predefinable tolerance range, for example, 100%±10%, the preservation regulation is reactivated (and the $CO_2$ removal target is possibly increased again at the same time).

The preservation regulation reactivated on the basis of a moving out of the tolerance range remains active until the trend parameter $etCO_2equal$, which continues to be determined currently, has once reached the set point, i.e., for example, 100%, or until currently determined trend parameters $etCO_2equal$ remain within the tolerance range or within a preservation regulation tolerance range that is "narrower" than the tolerance range, for example, 100%+2%, 100%+3%, 100%+5%, etc., during a predefined or predefinable time period. The preservation regulation is then deactivated again automatically, and the reduction of the removal target for the $CO_2$ removal ($CO_2Rt$) by the above-mentioned predefined or predefinable value and starting from the value for the $CO_2$ removal target valid during the deactivation of the preservation regulation starts again.

A multiple switching may take place between the reduction of the $CO_2$ removal target ($CO_2Rt$) and the automatic reactivation of the preservation regulation during the operation of the system 10 in the weaning mode.

Figure 4:
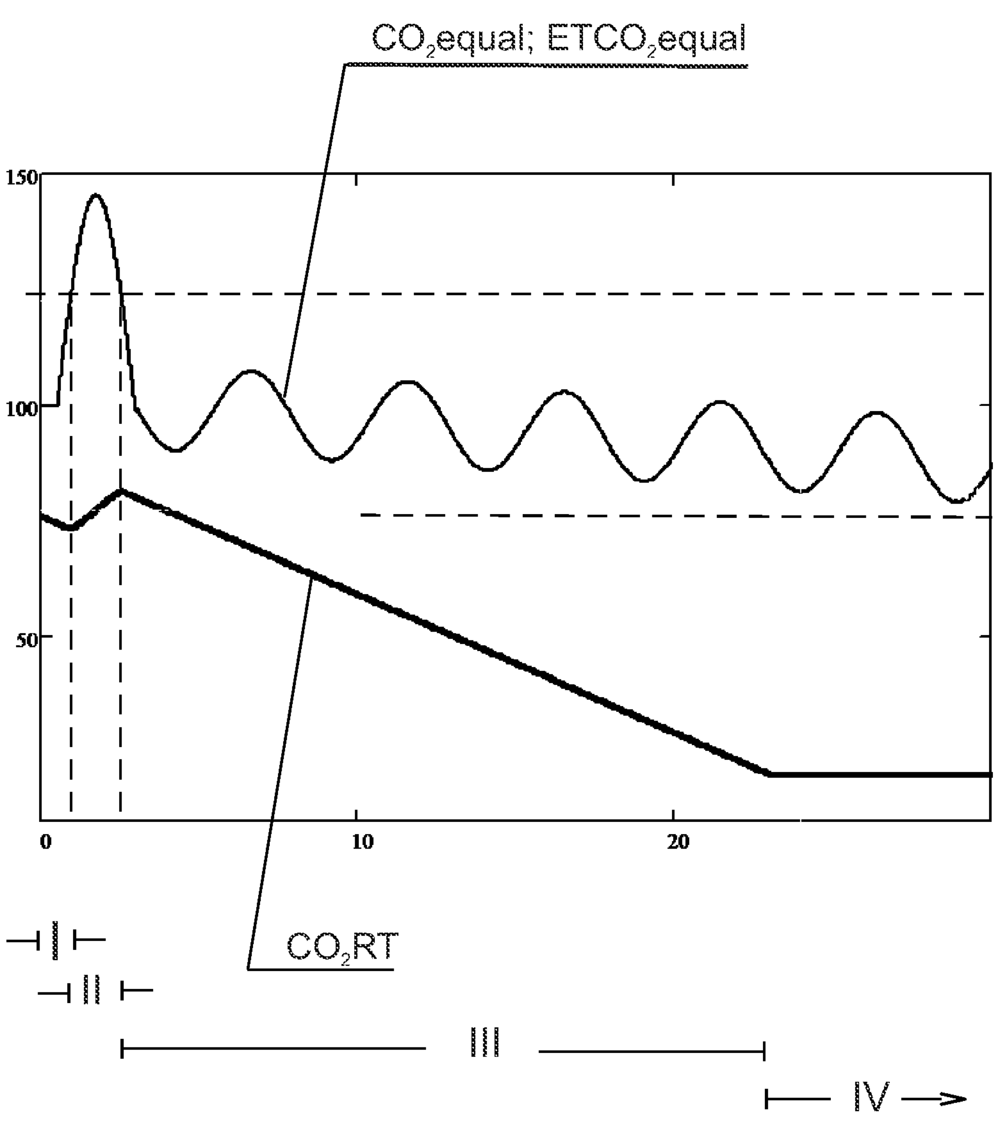
FIG. 4 is a schematic view of a curve describing the weaning of a patient from an extracorporeal blood gas exchange.

The view in FIG. 4 shows as a function of the time t plotted in hours a possible curve of weaning, namely, a curve of the trend parameter ($etCO_2equal$) in the upper area and a curve of the $CO_2$ removal target ($CO_2Rt$) in the lower area. The value range of the curve of the trend parameter is plotted on the ordinate in percentage values (50%, 100%, 150%). The value range of the curve of the $CO_2$ removal target ($CO_2Rt$) is not shown additionally on the ordinate. The graph of the $CO_2$ removal target starts in the example shown at 80 mL/minute and ends at 20 mL/minute.

According to the situation shown as an example in FIG. 4, the weaning mode is activated at the time t=0. The $CO_2$ removal target drops at first (time period I) correspondingly. The trend parameter $etCO_2equal$, which continues to be determined, does, however, rise and increase so much that it moves beyond an upper limit of a tolerance range, which is shown by two horizontal broken lines and is marked here as an example at 100%±25%. The width of the tolerance range is predefined or predefinable and optionally adjustable. The tolerance range does not necessarily have to extend symmetrically around 100%. In case of a moving out of the tolerance range, the preservation regulation is reactivated. This brings about in the example shown a rise in the $CO_2$ removal target (time period II). The reactivation of the preservation regulation ends in the example shown with the return of the trend parameter $etCO_2equal$ into the tolerance range.

Other criteria for the ending of the reactivated preservation regulation are likewise possible alternatively (see above). After the preservation regulation has been again deactivated, the reduction of the $CO_2$ removal target ($CO_2Rt$) begins again. The reduction lasts during the time period III and ends when the $CO_2$ removal target ($CO_2Rt$) reaches a predefined or predefinable lower limit value. The $CO_2$ removal device 16 subsequently continues to operate with the $CO_2$ removal target reached last until the $CO_2$ removal device 16 is deactivated and removed by the operator of the system 10.

Figure 5:
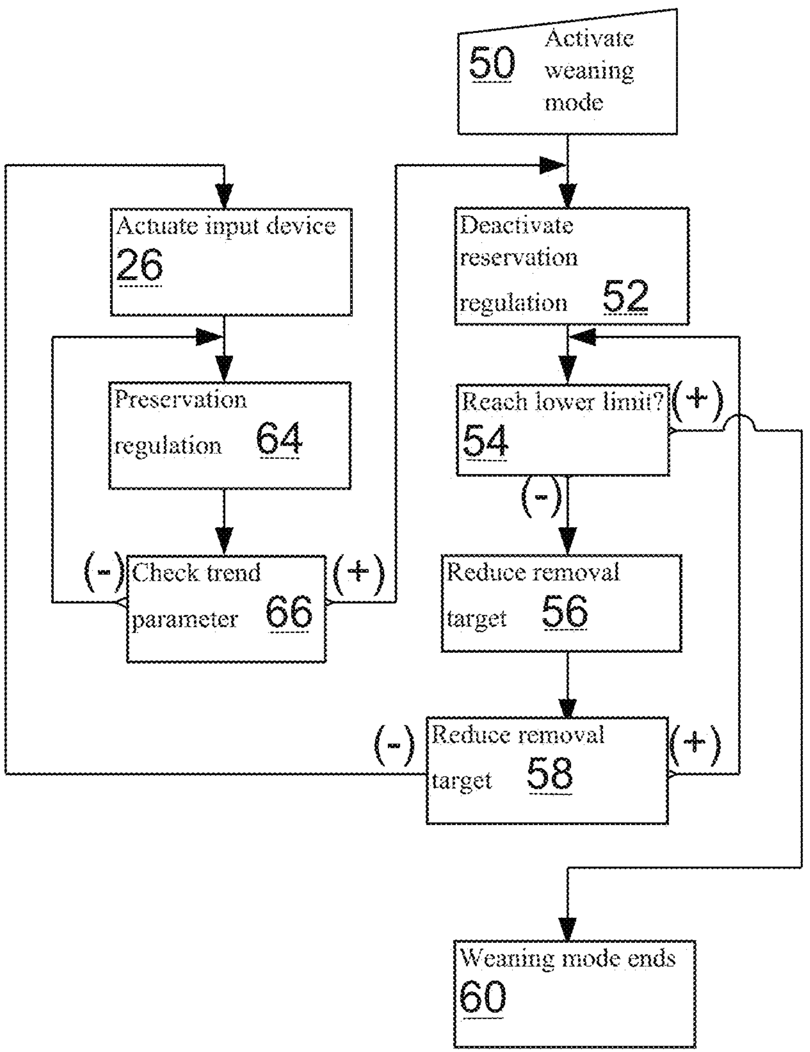
FIG. 5 is a flow chart for illustrating a process taking place during the weaning according to FIG. 4.

The view in FIG. 5 illustrates the weaning mode as was described above on the basis of a schematically simplified flow chart.

The weaning mode is activated by an operating action of a user (block 50). The preservation regulation is deactivated at first (block 52) in the weaning mode. It is then checked (block 54) whether a $CO_2$ removal target ($CO_2$ Rt) to be reduced in the weaning mode has already reached a predefined or predefinable lower limit value. This cannot normally be the case immediately after the activation of the weaning mode. The condition is not consequently met normally and carrying out of the "minus" branch will correspondingly follow and the $CO_2$ removal target is subsequently reduced (block 56). It is then checked (block 58) whether the trend parameter is still within the tolerance range. As long as this is the case ("plus" branch), the process is branched off before block 54. It is checked there whether the lower limit value for the $CO_2$ removal target has already been reached (block 54), and as long as it is not the case, the removal target is reduced (block 56) and the trend parameter is then checked relative to the tolerance range (block 58). As long as the trend parameter remains in the tolerance range and the limit value for the $CO_2$ removal target is not yet reached, the $CO_2$ removal target is reduced by means of this partial functionality, and the view in the schematically simplified flow chart does not take into consideration the circumstance that the reduction preferably takes place at a predefined rate of reduction per unit of time, for example, 3 mL/minute per hour. When it is determined during the reduction of the $CO_2$ removal target (block 54) that the limit value for the $CO_2$ removal target is reached, the weaning mode ends (block 60) and the $CO_2$ removal target is not reduced further. It may, however, happen during the reduction of the $CO_2$ removal target (blocks 54, 56, 58) that a checking of the trend parameter in relation to the tolerance range (block 58) reveals that the trend parameter has left the tolerance range. The preservation regulation is then activated ("minus" branch) and the preservation regulation is subsequently carried out (block 64). It is checked during the action of the preservation regulation (block 66) whether the trend parameter meets a predefined or predefinable quality criterion. The quality criterion may be defined, for example, such that the trend parameter must have returned again into the tolerance range, it must have reached a predefined or predefinable value, for example, 100%, at least once, or the like (see above). When this happens ("plus" branch), the process is branched off for the renewed deactivation of the preservation regulation (block 52), and the reduction of the $CO_2$ removal target will then begin again. As long as the trend parameter does not meet the quality criterion ("minus" branch), the preservation regulation (block 64) is carried out.

Whenever predefined or predefinable values are mentioned above, these are preferably basically variable data, which are stored in the memory 32 of the control unit 22 and the frameworks of the execution of the process or of individual embodiments of the process are automatically accessed. Predefined values are selected, for example, at the time of delivery or during the first use of the control unit 22 and loaded into the memory 32. Predefinable values are values that can also be changed, for example, during the operation of the control unit 22 or between consecutive uses of the control unit 22 by an operator of the control unit 22 or by an operator of the system 10, especially a physician, in terms of a parameterization.

Individual prominent aspects of the description being submitted here can thus be briefly summarized as follows: Proposed are a system 10 for supporting the blood gas exchange of a patient 12 by means of a ventilator 14 as well as by means of a $CO_2$ removal device 16, and a process for operating such a system 10, wherein a measured value concerning an expiratory or end-expiratory $CO_2$ concentration in the breathing gas of the patient 12 can be detected by means of a sensor system 20, wherein the respective current measured value can be optionally outputted to a display unit 24, wherein a measured value can be selected as a start value by means of an operating action, for example, in the course of an observation of the display of the display unit 24, wherein, for example, a trend parameter can be determined with the start value and with a respective, currently determined measured value, and wherein a difference of a set point for the trend parameter and a respective current value of the trend parameter can be fed to a controller 42, which acts on the $CO_2$ removal device 16.

While specific embodiments of the invention have been shown and described in detail to illustrate the application of the principles of the invention, it will be understood that the invention may be embodied otherwise without departing from such principles.

LIST OF REFERENCE NUMBERS

- 10 System
- 12 Patient
- 14 Medical device, ventilator
- 16 Medical device, $CO_2$ removal device
- 18 Breathing mask
- 20 Sensor system
- 22 Medical device, control unit
- 24 Display unit
- 26 Input device
- 30 Processing unit
- 32 Memory
- 34 Control program
- 36 Start value storage location
- 40 Control circuit
- 42 Controller
- 44 Start value
- 46 Standardizing unit
- 50-66 Block (in flow chart)

The invention claimed is:

1. A system for supporting a blood gas exchange of a patient by ventilation as well as by extracorporeal blood gas exchange by $CO_2$ removal, the system comprising:

a medical device comprising a ventilator;

a medical device comprising a $CO_2$ removal device for the extracorporeal blood gas exchange;

a controller configured to act on the $CO_2$ removal device; and a sensor system configured to detect a current measured value concerning an expiratory $CO_2$ concentration in the breathing gas of the patient, wherein the current measured value is selectable as a start value by an operating action at the system, and wherein:

the controller receiving a difference between a trend parameter and a setpoint for the trend parameter, the trend parameter corresponding to a $CO_2$ content of blood of the patient;

the trend parameter is a quotient of the current measured value of the expiratory $CO_2$ concentration in the breathing gas of the patient and the start value of the expiratory $CO_2$ concentration in the breathing gas of the patient;

the controller acts on the $CO_2$ removal device.

2. The system in accordance with claim 1, wherein the sensor system is further configured to detect an end-expiratory $CO_2$ concentration in the breathing gas of the patient as the measured value concerning the expiratory $CO_2$ concentration in the breathing gas of the patient.

3. The system in accordance with claim 1, wherein the trend parameter is determined with the start value and with the measured value which is currently determined, and wherein a difference of a set point for the trend parameter and the respective current value of the trend parameter is fed to the controller, which acts on the $CO_2$ removal device.

4. The system in accordance with claim 3, wherein the trend parameter is determined as a standardization of the current measured value in relation to the start value.

5. The system in accordance with claim 1, further comprising a display unit, wherein the measured value currently determined is outputted at the display unit and the displayed measured value is selected as the start value by the operating action.

6. The system in accordance with claim 1, wherein a spontaneous respiratory rate of the patient is monitored by the sensor system and a signal element is actuated in case a predefined or predefinable threshold value is exceeded.

7. The system in accordance with claim 1, wherein a weaning mode is activated by means of an operating action on the system, and wherein a $CO_2$ removal target is reduced automatically and in a controlled manner in the weaning mode.

8. The system in accordance with claim 7, wherein an influence of the controller on the $CO_2$ removal device is deactivated at a beginning of the reduction of the $CO_2$ removal target, wherein the trend parameter is monitored in relation to a predefined or predefinable tolerance range during the reduction of the $CO_2$ removal target, and wherein the influence of the controller on the $CO_2$ removal device is reactivated in case of a moving out of the tolerance range, and the reduction of the $CO_2$ removal target is deactivated.

9. A process for operating a system for supporting a blood gas exchange of a patient by ventilation as well as by extracorporeal blood gas exchange by a $CO_2$ removal wherein the system comprises: a medical device comprising a ventilator; a medical device comprising a $CO_2$ removal device for the extracorporeal blood gas exchange; a controller configured to act on the $CO_2$ removal device; and a sensor system configured to detect a current measured value concerning an expiratory $CO_2$ concentration in the breathing gas of the patient, and wherein the current measured value is selectable as a start value by an operating action at the system wherein a difference of a trend parameter formed with the start value and a set point for the trend parameter is fed to the controller, the controller acting on the $CO_2$ removal device, the process comprising the steps of:

detecting the current measured value concerning the expiratory $CO_2$ concentration in the breathing gas of the patient by means of the sensor system;

selecting the measured value which is current as the start value by means of the operating action at the system; and feeding the difference between the trend parameter and the set point for the trend parameter to the controller, the trend parameter being a quotient of the current measured value of the expiratory $CO_2$ concentration in the breathing gas of the patient and the start value of the expiratory $CO_2$ concentration in the breathing gas of the patient, the controller acting on the $CO_2$ removal device, the trend parameter corresponding to a $CO_2$ content of blood of the patient.

10. The process in accordance with claim 9, wherein the trend parameter is determined with the start value and the current measured value, and wherein the difference of the set point for the trend parameter and the trend parameter currently determined is fed to the controller, which acts on the $CO_2$ removal device.

11. The process in accordance with claim 10, wherein the trend parameter is determined as a standardization of the current measured value in relation to the start value.

12. The process in accordance with claim 9, wherein the current measured value is outputted on a display unit and a displayed measured value is selected as the start value by the operating action.

13. The process in accordance with claim 9, wherein a spontaneous respiratory rate of the patient is monitored by the sensor system and a signal element is actuated in case a predefined or predefinable threshold value is exceeded.

14. The process in accordance with claim 9, wherein a weaning mode is activated by means of the operating action on the system, and wherein a $CO_2$ removal target is reduced automatically and in a controlled manner in the weaning mode.

15. The process in accordance with claim 14, wherein an influence of the controller on the $CO_2$ removal device is deactivated at a beginning of the reduction of the $CO_2$ removal target, wherein the trend parameter is monitored in reference to a predefined or predefinable tolerance range during the reduction of the $CO_2$ removal target and wherein the influence of the controller on the $CO_2$ removal device is reactivated and the reduction of the $CO_2$ removal target is deactivated, on the other hand, in case of a moving out of the tolerance range.

16. The process according to claim 9, further comprising confirming a presence of an acceptable $CO_2$ concentration in the breathing gas by an operator of the system by the operating action;

regulating operation of the $CO_2$ removal device to or toward a $CO_2$ concentration characterized as being acceptable upon such the operating action and wherein removal of carbon dioxide from the blood of the patient is carried out during the regulated operation of the $CO_2$ removal device.

17. The process according to claim 9, wherein a computer program with program code is provided to carry one or more of the steps with the control program run by a processing unit in one or more of the medical devices.

18. The system in accordance with claim 1, wherein one or both of the medical devices provide a processor configured for:

detecting the current measured value concerning the expiratory $CO_2$ concentration in the breathing gas of the patient by means of the sensor system;

selecting the current measured value which is current as the start value by means of the operating action at the system; and feeding:

the difference of the start value and the current measured value to the controller, which acts on the $CO_2$ removal device; or a difference of the trend parameter formed with the start value and the set point for the trend parameter to the controller, which acts on the $CO_2$ removal device.

19. The process in accordance with claim 9, wherein the sensor system is further configured to detect the current measured value concerning the expiratory $CO_2$ concentration in the breathing gas of the patient comprises an end-expiratory $CO_2$ concentration in the breathing gas of the patient.

20. A process for operating a system for supporting a blood gas exchange of a patient by ventilation as well as by extracorporeal blood gas exchange by a $CO_2$ removal, the process comprising:

providing the system comprising: a medical device comprising a ventilator; a medical device comprising a $CO_2$ removal device for the extracorporeal blood gas exchange; a controller configured to act on the $CO_2$ removal device; and a sensor system configured to detect a current measured value concerning an expiratory $CO_2$ concentration in the breathing gas of the patient, and wherein the current measured value is selectable as a start value by an operating action at the system wherein a difference of a trend parameter formed with the start value and a set point for the trend parameter is fed to the controller, the controller acting on the $CO_2$ removal device;

detecting a measured value concerning an expiratory $CO_2$ concentration in the breathing gas of the patient by means of the sensor system;

selecting the measured value which is current as the start value by means of an operating action at the system; and feeding a difference between a trend parameter and a setpoint for the trend parameter to the controller, the trend parameter being a quotient of a currently determined measured value of the expiratory $CO_2$ concentration in the breathing gas of the patient and the start value of the expiratory $CO_2$ concentration in the breathing gas of the patient, the controller acting on the $CO_2$ removal device, the trend parameter corresponding to a $CO_2$ content of blood of the patient.

* * * * *